(12) United States Patent
Fujioka

(10) Patent No.: US 7,608,068 B2
(45) Date of Patent: Oct. 27, 2009

(54) DISPOSABLE PANTS

(75) Inventor: Masaru Fujioka, Tokushima (JP)

(73) Assignee: Livedo Corporation, Ehime (JP)

( * ) Notice: Subject to any disclaimer, the term of this patent is extended or adjusted under 35 U.S.C. 154(b) by 12 days.

(21) Appl. No.: 11/795,020

(22) PCT Filed: Jan. 17, 2006

(86) PCT No.: PCT/JP2006/300497

§ 371 (c)(1),
(2), (4) Date: Jul. 10, 2007

(87) PCT Pub. No.: WO2006/077814

PCT Pub. Date: Jul. 27, 2006

(65) Prior Publication Data

US 2008/0091163 A1 Apr. 17, 2008

(30) Foreign Application Priority Data

Jan. 19, 2005 (JP) .............................. 2005-011428

(51) Int. Cl.
*A61F 13/15* (2006.01)
*A61F 13/20* (2006.01)
(52) U.S. Cl. .................... 604/385.11; 604/385.04; 604/385.01; 604/389; 604/391; 604/394
(58) Field of Classification Search ............ 604/385.04, 604/385.01, 396, 389, 391, 385.11
See application file for complete search history.

(56) References Cited

U.S. PATENT DOCUMENTS 5,560,798 A * 10/1996 Brusky ....................... 156/277

| | | |
|---|---|---|
| 5,897,546 A | 4/1999 | Kido et al. |
| 6,524,294 B1 * | 2/2003 | Hilston et al. ............... 604/386 |

(Continued)

FOREIGN PATENT DOCUMENTS

| | | |
|---|---|---|
| DE | 202 20 237 | 3/2003 |
| JP | 5-317356 | 12/1993 |
| JP | 07-328069 | 12/1995 |
| JP | 9-38139 | 2/1997 |
| JP | 2001-258938 | 9/2001 |

(Continued)

OTHER PUBLICATIONS

Extended European Search Report issued Aug. 5, 2009 in connection with corresponding European Application No. 06 71 1777.

*Primary Examiner*—Tatyana Zalukaeva
*Assistant Examiner*—Susan Su
(74) *Attorney, Agent, or Firm*—Wenderoth, Lind & Ponack, L.L.P.

(57) ABSTRACT

The present invention provides disposable pants achieving improved workability in putting on and taking off by increasing the visibility of tabs on adhesive pieces. The disposable pants include a front abdominal section and a rear section joined almost annularly, and a crotch section provided to be joined between the front abdominal section and rear section. Left and right breaking parts are provided on the front abdominal section for breaking the front abdominal section. Left and right adhesive pieces are bonded to laterally outward sides of the left and right breaking parts in the front abdominal section. An adhesive part to/from which the left and right adhesive pieces are attached/detached is provided between the left and right breaking parts on the exterior side of the front abdominal section. The left and right adhesive pieces are provided with tabs for attachment/detachment to/from the adhesive part, and the tabs are provided with tab identification marks for identification from neighboring members.

17 Claims, 10 Drawing Sheets

U.S. PATENT DOCUMENTS

| | | | |
|---|---|---|---|
| 7,077,834 B2 * | 7/2006 | Bishop et al. | 604/385.11 |
| 2002/0065503 A1 | 5/2002 | Guidotti | |
| 2002/0148557 A1 * | 10/2002 | Heller et al. | 156/252 |
| 2003/0051805 A1 | 3/2003 | Mlinar et al. | |
| 2003/0055389 A1 * | 3/2003 | Sanders et al. | 604/358 |
| 2003/0100879 A1 * | 5/2003 | Kline et al. | 604/386 |
| 2004/0015144 A1 | 1/2004 | Mori et al. | |
| 2004/0097896 A1 * | 5/2004 | Raufman et al. | 604/385.01 |
| 2005/0192553 A1 * | 9/2005 | Hasler et al. | 604/385.11 |
| 2008/0114322 A1 * | 5/2008 | Schmoker et al. | 604/385.03 |

FOREIGN PATENT DOCUMENTS

| | | |
|---|---|---|
| JP | 2002-17778 | 1/2002 |
| JP | 2002-209936 | 7/2002 |
| JP | 2003-290286 | 10/2003 |
| JP | 2004-261354 | 9/2004 |
| WO | 03/003960 | 1/2003 |
| WO | 03/024372 | 3/2003 |

* cited by examiner

F I G. 5
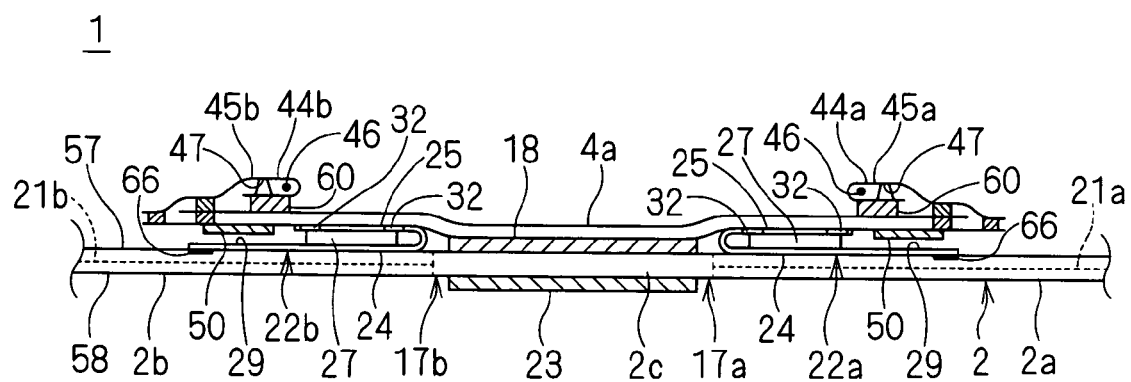

DISPOSABLE PANTS

TECHNICAL FIELD

The present invention relates to disposable pants usable as both pants and a diaper.

BACKGROUND ART

As conventional disposable pants of this type, there is a technique described in Japanese Patent Application Laid-Open No. 5-317356. In the pants, breaking lines are provided on both left and right sides of a front section to allow the front section to be separated at the breaking lines, and adhesive pieces are provided at bonded parts on the left and right sides of the front section and a rear section. When the front section is separated at the breaking lines, the front section and rear section are fastened by the left and right adhesive pieces.

The pants disclosed in the above-mentioned gazette, however, are typically made of materials of similar colors such as white, for example, as a whole, and thus, when used as a diaper after developed at the breaking lines, it is difficult to visually identify tabs of adhesive pieces from other members as they have a similar color to the other members, resulting in the problem of poor workability.

DISCLOSURE OF INVENTION

To solve the above problem, the present invention has an object to provide disposable pants achieving improved workability in putting on and taking off by increasing the visibility of tabs on adhesive pieces.

Disposable pants according to a first aspect of the present invention comprise a front abdominal section and a rear section joined almost annularly, and a crotch section provided to be joined between the front abdominal section and rear section, said crotch section being provided with an absorber, left and right breaking parts for breaking said front abdominal section being provided on both left and right sides of an area of said front abdominal section to which said crotch section is joined. Left and right adhesive pieces are bonded to laterally outward sides of said left and right breaking parts in said front abdominal section. An adhesive part to/from which said left and right adhesive pieces are attached/detached is provided between said left and right breaking parts on an exterior side of said front abdominal section. The left and right adhesive pieces are each provided with a tab for attachment/detachment to/from said adhesive part as well as a tab identification mark.

According to this aspect, the tab identification mark is provided for distinguishing the tab provided for each of the adhesive pieces from other members. The position of the tabs is thus easily identified by the tab identification mark, achieving easy and quick attachment/detachment of the adhesive pieces to/from the adhesive part, and improved workability in attaching/detaching.

According to a second aspect of the invention, the tab identification mark has a color different from other members.

This aspect can easily be achieved by using a tab of different color from other members or coloring the tab differently from other members.

According to a third aspect of the invention, the color of the tab identification mark is given by coloring.

This aspect can easily be achieved by coloring the tab.

According to a fourth aspect of the invention, the tab identification mark is made of a colored adhesive for adhering and fixing, to the tab, an adhesive member to be attached/detached to/from the adhesive part.

According to this aspect, the tab identification mark can be provided concurrently with the step of adhering the adhesive members to the adhesive part, advantageously achieving excellent production efficiency.

According to a fifth aspect of the invention, the tab identification mark has a color different from other members, and is made of an adhesive member fixed to the tab to be attached/detached to/from the adhesive part.

According to this aspect, the tab identification mark can be obtained concurrently with the step of adhering the adhesive members to the adhesive part, advantageously achieving excellent production efficiency.

BRIEF DESCRIPTION OF DRAWINGS

FIG. 5 is a sectional view taken along a line C1-C1 of the disposable pants shown in FIG. 1.

DETAILED DESCRIPTION OF THE INVENTION

FIRST EMBODIMENT

<General Description>

Figure 1:
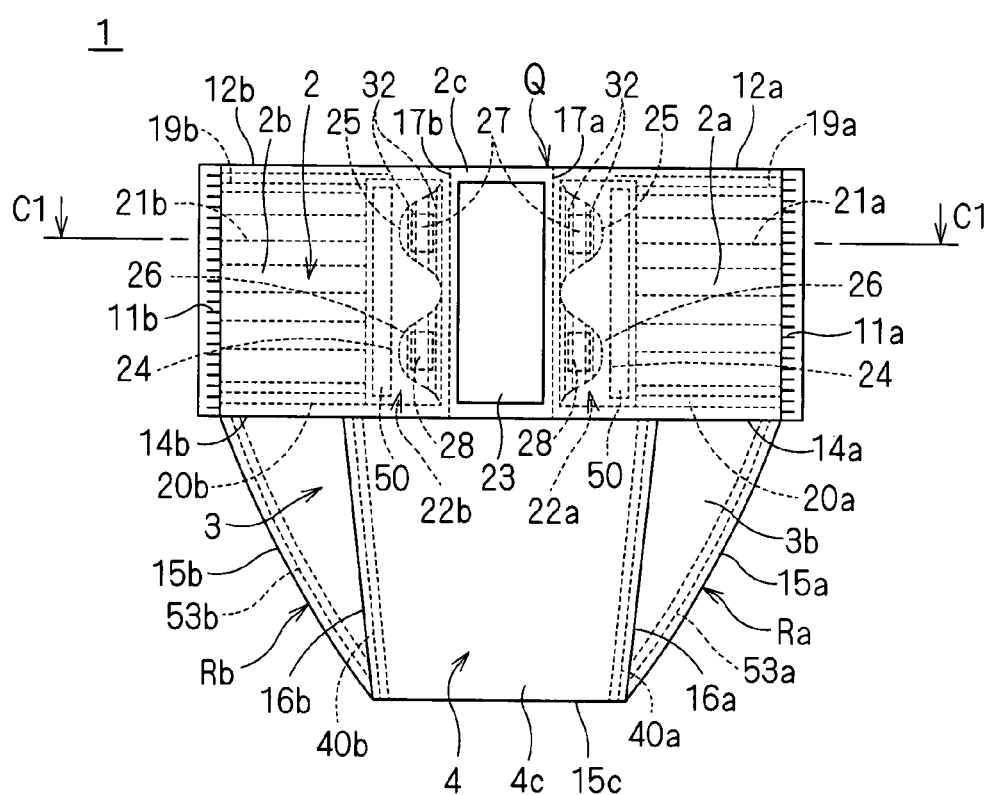
FIG. 1 is a front view of disposable pants according to a first embodiment of the present invention.

With reference to FIGS. 1 to 8, disposable pants 1 according to a first embodiment of the present invention will be described. This first embodiment will be described to a form in which adhesive pieces 22a and 22b are provided on the interior side of a front abdominal section 2. The disposable pants 1 are configured to comprise a front abdominal section 2 and a rear section 3 joined almost annularly and a crotch section 4 provided to be joined between the front abdominal section 2 and rear section 3, and are usable as both pants and a diaper. In the description of the disposable pants 1, the left and right shall indicate the left hand side and right hand side as viewed from a wearer.

The front abdominal section 2 and rear section 3 refer to portions of the disposable pants 1 that mainly face a front abdominal area and an area on the back of a wearer, respectively. Left and right edges of the front abdominal section 2 and left and right edges of the rear section 3 are bonded to each other, and the front abdominal section 2 and rear section 3 are thereby joined almost annularly. Accordingly, a left side bonded part 11a and a right side bonded part 11b for bonding the left and right edges of the front abdominal section 2 and left and right edges of the rear section 3 are formed on left and right edges of the disposable pants 1. Bonding at these side bonded parts 11a and 11b is created either by bonding with an adhesive such as a hot melt adhesive or ultrasonic welding (or heating welding), or by both of them in combination.

The crotch section 4 indicates a portion of the disposable pants 1 that mainly faces the crotch of a wearer, having a front crotch part 4a and a rear crotch part 4b joined to the front abdominal section 2 and rear section 3, respectively. In this embodiment, the front crotch part 4a and rear crotch part 4b of the crotch section 4 are bonded to the front abdominal section 2 and rear section 3 by an adhesive such as a hot melt adhesive. As a variation, the crotch section 4 may be formed integrally by a member connected to one or both of the front abdominal section 2 and rear section 3.

A waist opening Q is formed by upper edges 12a, 12b and 13 of the front abdominal section 2 and rear section 3 joined almost annularly as described. A left leg opening Ra is formed by a lower edge 14a of a left front abdominal part 2a of the front abdominal section 2, a sloped edge 15a on the left lower side of the rear section 3 and a left edge 16a of the crotch section 4. A right leg opening Rb is formed by a lower edge 14b of a right front abdominal part 2b of the front abdominal section 2, a sloped edge 15b on the right lower side of the rear section 3 and a right edge 16b of the crotch section 4.

<Front Abdominal Section>

The front abdominal section 2 is of almost laterally-long rectangular shape in plan view as an overall configuration (cf. FIG. 1), and includes the left front abdominal part 2a, right front abdominal part 2b and a central front abdominal part 2c positioned midway between them. A left breaking part 17a extending vertically through the front abdominal section 2 is formed between the left front abdominal part 2a and central front abdominal part 2c, and a right breaking part 17b extending vertically through the front abdominal section 2 is formed between the right front abdominal part 2b and central front abdominal part 2c. A bonding part 18 to the front crotch part 4a of the crotch section 4 is formed in the central front abdominal part 2c (cf. FIG. 5). Bonding at the bonding part 18 is created with an adhesive such as a hot melt adhesive.

The left and right breaking parts 17a and 17b are formed in the inner positions from both side edges of the front crotch part 4a. Here, the adhesive pieces 22a and 22b are attached to the respective front abdominal parts 2a and 2b in a folded manner in the inner side from both side edges of the front crotch part 4a, and the left and right breaking parts 17a and 17b are formed so as to extend along the inner side edges of these adhesive pieces 22a and 22b as folded. The respective breaking parts 17a and 17b are linear parts weakened as compared to areas therearound, and are formed, for example, by subjecting the front abdominal section 2 to linear heating (e.g., heat sealing), or intermittent cutting to provide perforations, or linear ultrasonic treatment (e.g., ultrasonic sealing).

Figure 2:
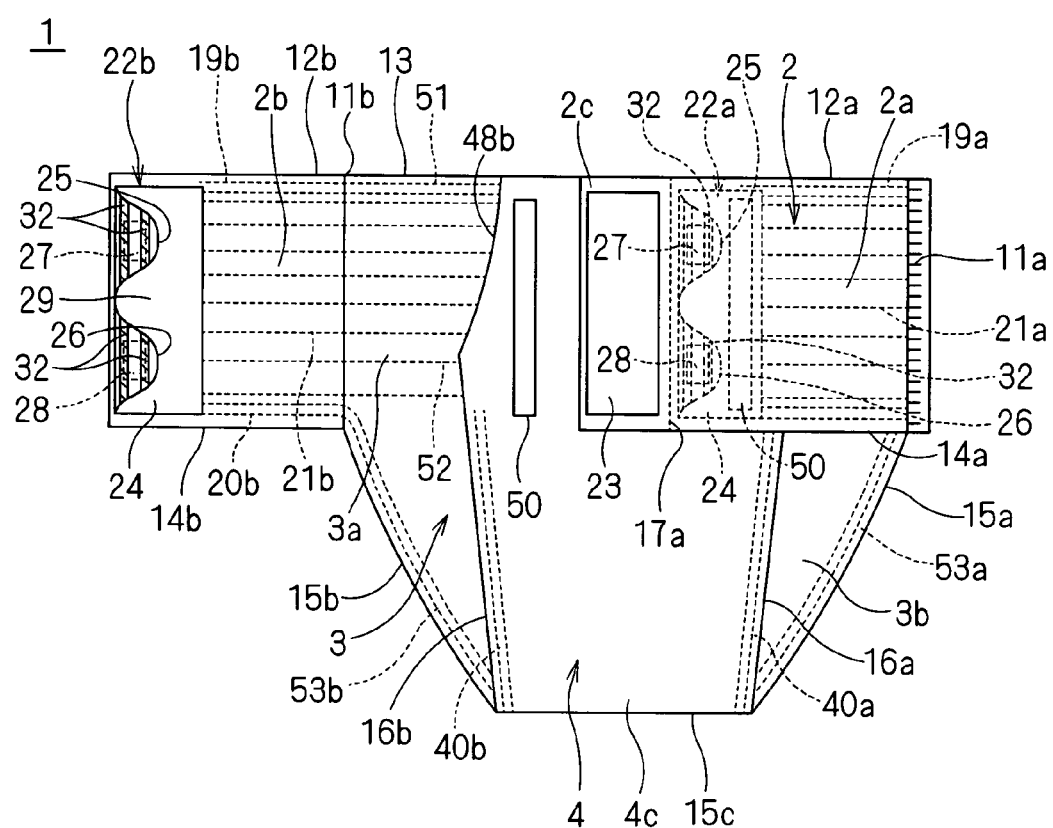
FIG. 2 is a diagram showing the state in which a right breaking part of the disposable pants shown in FIG. 1 is broken to develop a right front abdominal part.
Figure 3:
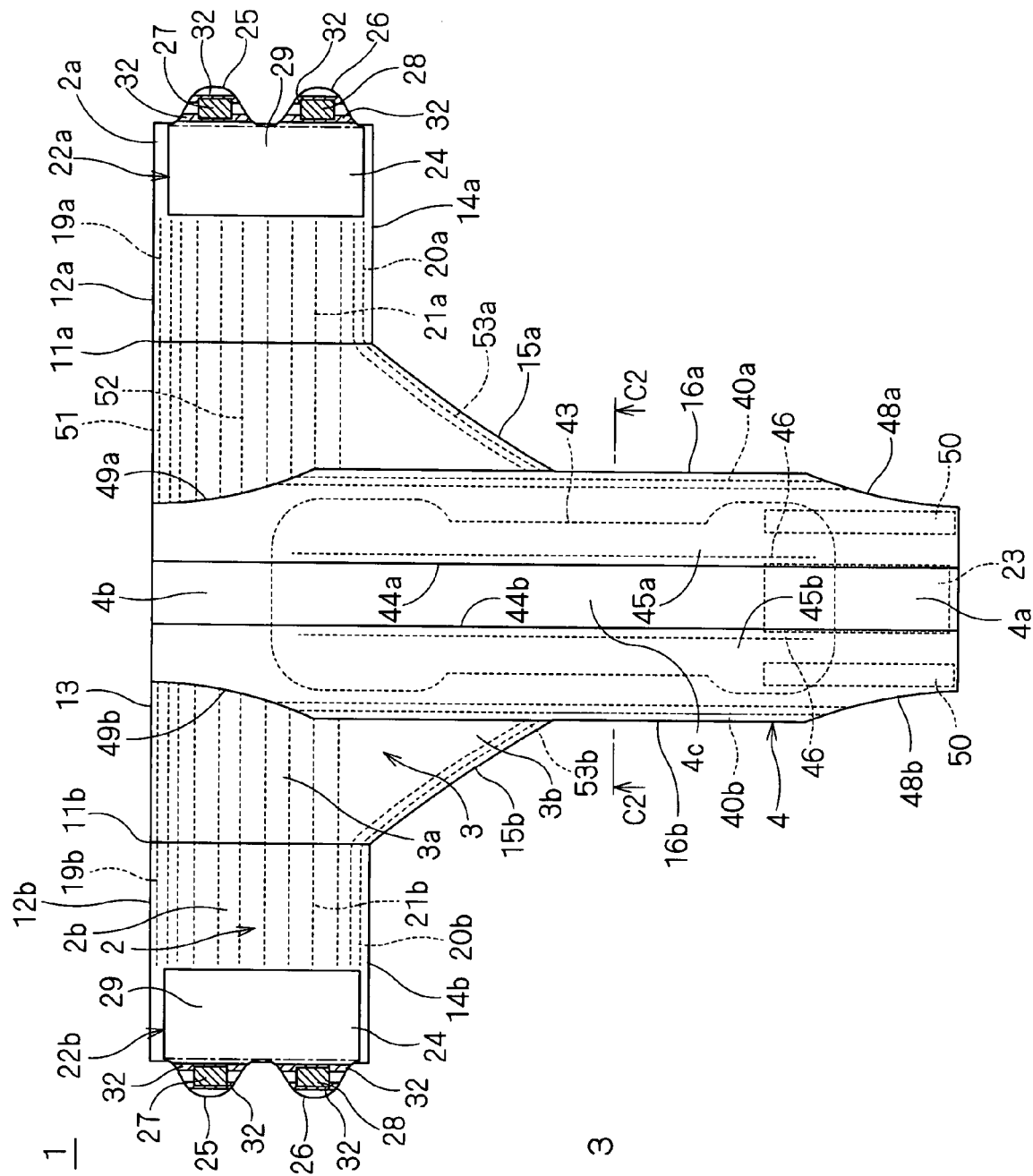
FIG. 3 is a diagram showing the state in which a left breaking part of the disposable pants shown in FIG. 2 is broken to develop a left front abdominal part as well as a crotch section.
Figure 4:
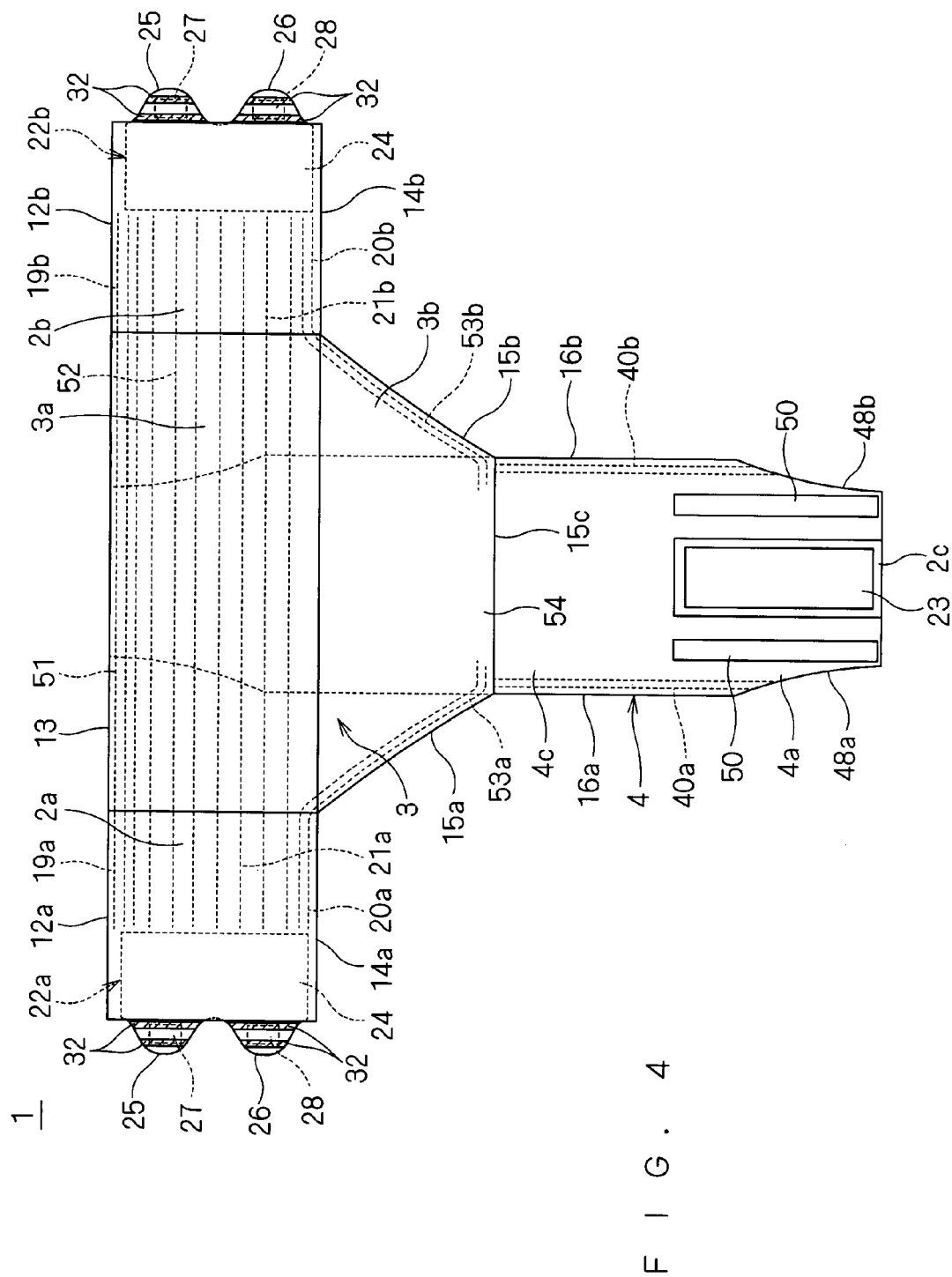
FIG. 4 is a diagram of the disposable pants shown in FIG. 3 as viewed from the opposite side to FIG. 3.

By breaking these breaking parts 17a and 17b, the front abdominal section 2 can be separated at the breaking parts 17a and 17b (cf. FIGS. 2 to 4). The front abdominal section 2 is thereby divided into the central front abdominal part 2c almost in the center and the front abdominal parts 2a, 2b on the left and right thereof at the position to which the crotch section 4 is joined. The breaking parts 17a and 17b may be formed linearly or may be formed as curved lines according to necessity. Alternatively, a plurality of linearly weakened parts may be formed in parallel to constitute each of the breaking parts 17a and 17b.

Waist elastic members 19a and 19b are attached in a laterally stretched state to the upper edges 12a and 12b of the left front abdominal part 2a and right front abdominal part 2b.

Leg elastic members 20a and 20b are attached in a laterally stretched state to the lower edges 14a, 14b of the left front abdominal part 2a and right front abdominal part 2b. Body elastic members 21a and 21b are attached in a laterally stretched state to areas between the upper edges 12a and 12b and lower edges 14a and 14b of the left front abdominal part 2a and right front abdominal part 2b. Contraction and stretch of these elastic members 19a, 19b, 20a, 20b, 21a and 21b allows the front abdominal section 2 (particularly, left front abdominal part 2a and right front abdominal part 2b) to fit snugly about the wearer's abdominal area.

Such front abdominal section 2 is formed by sandwiching the elastic members 19a, 19b, 20a, 20b, 21a and 21b between an interior-layer sheet 57 on the skin-facing side and an exterior-layer sheet 58 on the exterior side (cf. FIGS. 1 and 5).

Almost sheet-like left adhesive piece 22a and right adhesive piece 22b are bonded to the edges of the left front abdominal part 2a and right front abdominal part 2b on the interior side and on the side of the central front abdominal part 2c by an adhesive such as a hot melt adhesive (cf. FIGS. 1 to 5).

This adhesive piece 22a, 22b is provided on the interior side of the left front abdominal part 2a and right front abdominal part 2b in the form of pants before separating at the breaking parts 17a and 17b. Besides, portions of the adhesive pieces 22a and 22b that extend beyond the breaking parts 17a and 17b (here, tabs 25 and 26 which will be described later) are folded to be folded back toward their base sides (cf. FIGS. 1 and 5).

Figure 7:
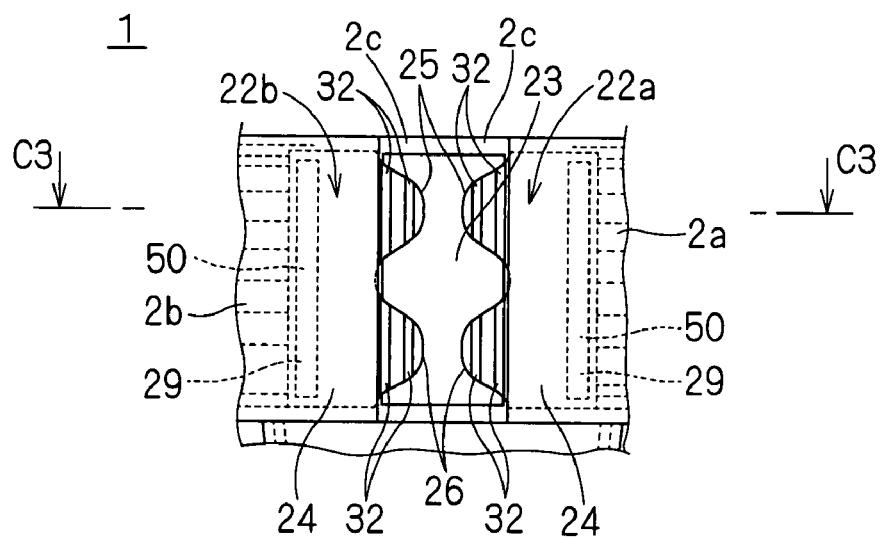
FIG. 7 is a diagram showing the state in which left and right tabs are attached to a central front abdominal part.
Figure 8:
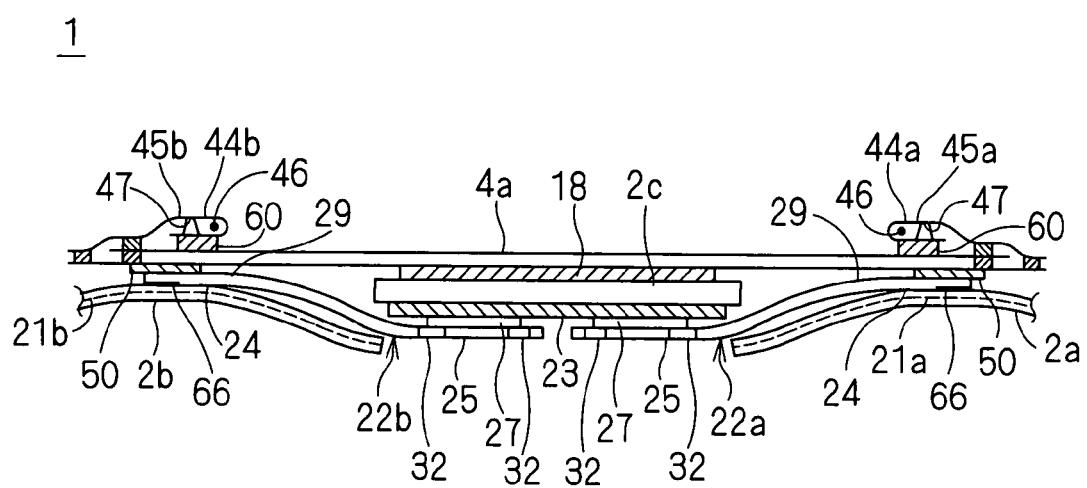
FIG. 8 is a sectional view taken along a line C3-C3 of the disposable pants shown in FIG. 7.

When breaking the breaking parts 17a and 17b for use as a diaper, the adhesive pieces 22a and 22b extend out from the edges of the left front abdominal part 2a and right front abdominal part 2b to be detachably attached to the exterior surface of an adhesive part 23 (cf. FIGS. 7 and 8).

That is, on the exterior side of the central front abdominal part 2c, the planar adhesive part 23 to which the adhesive pieces 22a and 22b are to be attached is provided. This adhesive part 23 has its width set at or smaller than the distance between the left and right breaking parts 17a and 17b (i.e., lateral dimension of central front abdominal part 2c) and its height set almost equal to the vertical dimension of the adhesive pieces 22a and 22b.

The adhesive pieces 22a and 22b each include an almost vertically long strip body 24 and two tabs 25 and 26 bifurcated one on top of the other extending from the body 24 toward its free edge side. The laterally outside edges of the body 24 are bonded to areas short of the edges of the left front abdominal part 2a and right front abdominal part 2b on their interior side and on the side of the breaking parts 17a and 17b by an adhesive 66, e.g., hot melt adhesive (cf. FIG. 5).

Adhesive members 27 and 28 are provided on the interior side (one side surface facing the adhesive part 23 in the form of diaper) of the respective tabs 25 and 26 of the adhesive pieces 22a and 22b. That is, the adhesive members 27 and 28 are attached and fixed to the interior side of the tabs 25 and 26 with an adhesive such as a hot melt adhesive. The respective tabs 25 and 26 extending from the body 24 of the adhesive pieces 22a and 22b are folded back, and the adhesive members 27 and 28 are directed to the exterior side of the front abdominal section 2. Further, the adhesive members 27 and 28 are provided in areas in the inner side from the outer edges of the adhesive pieces 22a and 22b. Here, as shown in FIG. 3, the adhesive members 27 and 28 are formed in almost square shape smaller than the respective tabs 25 and 26, and the adhesive members 27 and 28 are attached to one side surface of the respective tabs 25 and 26 so as not to overlap their outer edges. As shown in FIGS. 7 and 8, the respective adhesive pieces 22a and 22b are detachably attached to the adhesive part 23 with the adhesive members 27 and 28 interposed therebetween.

Further, as shown in FIGS. 1 to 4, provided near the leading ends and base sides of the respective tabs 25 and 26 are tab identification marks 32 so as to facilitate visual identification of the tabs 25 and 26 from the front abdominal section 2, adhesive part 23, body 24 and the like positioned therearound. For instance, in the present embodiment, the front abdominal section 2, rear section 3, crotch section 4, adhesive pieces 22a, 22b, adhesive part 23, adhesive members 27, 28, and the like mainly constituting the disposable pants 1 have similar colors such as white, for example, and the tab identification marks 32 are provided by linearly coloring the tabs 25 and 26 in green, for example, differently from other members by a pigment or the like using ink-jet type coloring means, for example, or linearly attaching a colored tape of green, for example, which is different from other members, to the tabs 25 and 26.

Furthermore, in the present embodiment, portions closer to the base sides than the adhesive members 27 and 28 of the interior surface of the adhesive pieces 22a and 22b (portions on the interior side of the body 24) are also formed as adhesive parts 29. Adhesive members 50 (or adhesive elements) which will be described later are also provided to be detachably attached to the adhesive parts 29 of the body 24 of each of the adhesive pieces 22a and 22b with the adhesive members 27 and 28 on the tabs 25 and 26 of the adhesive pieces 22a and 22b being attached to the aforementioned adhesive part 23 (cf. FIGS. 7 and 8).

Further, the other side surface (exterior surface) of the adhesive pieces 22a and 22b opposite to the surface on which the aforementioned adhesive members 27 and 28 are provided is also formed as an adhesive part. This adhesive part allows the aforementioned adhesive members 27 and 28 to be detachably attached thereto.

Then, in the state where one side adhesive piece 22a (or 22b) is attached to the adhesive part 23 with the adhesive members 27 and 28 interposed therebetween, the other side adhesive piece 22b (or 22a) can be attached so as to overlap the one side adhesive piece 22a (or 22b).

The region where the adhesive part on the exterior side of the adhesive pieces 22a and 22b is provided may be the whole or part of the other side surface of the adhesive pieces 22a and 22b, but the arrangement so as to include the tips of the tabs 25 and 26 brings a bigger advantage in easily fixing the adhesive pieces 22a and 22b securely while overlapping them with each other.

Specific examples of the adhesive parts 23, 29, and the like, may include a loop-side member having a nonwoven fabric, a woven fabric, a knitted material or the like with a fine loop structure being densely formed on its surface. Specific examples of the adhesive members 27, 28 and 50 may include a hook-side member with a fine hook structure in freely detachable engagement with the loop-side member being densely formed on its surface.

More specifically, as the adhesive parts 23, 29, and the like, a plastic film composite material having on its surface a nonwoven fabric, a woven fabric or the like which is suitably used as a loop-side member for a hook-and-loop fastener is used for example. As the adhesive parts 23, 29, and the like, a loop-side member may be attached as a separate member to the central front abdominal part 2c or the adhesive pieces 22a and 22b; alternatively, the exterior surface of the central front abdominal part 2c, or exterior or interior surface itself of the adhesive pieces 22a and 22b may be made to function as a loop-side member. For that purpose, for instance, as a material for the adhesive pieces 22a, 22b or the central front abdominal part 2c itself, one having a loop structure may be selected, or alternatively, required portions on the surfaces of the adhesive pieces 22a, 22b or the central front abdominal part 2c may be surface-treated to be fuzzed, or may further be treated, for example, by weaving wool into the adhesive pieces 22a, 22b or the central front abdominal part 2c to provide a loop structure.

As the adhesive members 27, 28, 50, a plastic film having pins densely formed on its surface which is suitably used as a hook-side member for a hook-and-loop fastener is used.

Another specific example of the adhesive parts 23, 29, and the like, may include a plastic film or the like, which is surface-treated by using PEELOIL, for example, so as to have repetitive removability from an adhesive. Still another specific example may include a reusable adhesive.

In the above-described specific examples of the aforementioned adhesive parts 23, 29, and the like, and those of the adhesive members 27, 28, 50, their structures may be replaced with each other.

Further, in the present embodiment, the adhesive members 27 and 28 are not provided on the tips of the respective tabs 25 and 26 of the adhesive pieces 22a and 22b for the purpose of easy lifting of the tabs 25 and 26 in attaching/detaching.

In this front abdominal section 2, when breaking at the respective breaking parts 17a and 17b, the right front abdominal part 2b is developed to the right integrally with the right adhesive piece 22b, and the left front abdominal part 2a is developed to the left integrally with the left adhesive piece 22a. At this time, the central front abdominal part 2c is kept bonded to the crotch section 4 and remains on the exterior side of the front crotch part 4a.

Accordingly, since the front abdominal section 2 and crotch section 4 are secured by the bonding part 18 in the state before breaking the breaking parts 17a and 17b (at the time of product shipping), the disposable pants 1 function as pants, and are easily raised/lowered similarly to typical disposable pants having no opening/closing means such as the adhesive pieces 22a and 22b, etc. (cf. FIG. 1).

Further, in the case where the disposable pants 1 are worn as pants and when an absorber 43 to be described later absorbs and contains bodily wastes, the breaking parts 17a and 17b are broken and developed, so that the pants 1 can easily be removed from the wearer. In this case, the pants 1 can be removed without taking off the wearer's garments.

Further, after breaking the breaking parts 17a and 17b and developing the front abdominal section 2 to see whether the inside of the pants 1 has been soiled, the respective tabs 25 and 26 of the adhesive pieces 22a and 22b may be developed and extended to be engaged with the adhesive part 23, so that the pants 1 can be returned to its original state as pants. Further, when the pants 1 and an optional pad such as a urine pad are used in combination, the adhesive pieces 22a and 22b can be attached/detached to allow replacing of such optional pad, and the like to be carried out easily.

Further, the pants 1 may be used as a typical disposable diaper by applying the pants 1 developed as shown in FIG. 3 before putting them on, around the wearer's hips and then closing them in the order of FIGS. 3, 2 and 1. In this case, the pants 1 can be put on and removed without taking off the wearer's garments.

Further, when in use with the breaking parts 17a and 17b being broken, the both adhesive pieces 22a and 22b may be attached so as to overlap each other in the case where the wearer has slim hips. That is, with the tabs 25 and 26 on one side adhesive piece 22a (or 22b) being attached to the adhesive part 23, the tabs 25 and 26 on the other side adhesive piece 22b (22a) may be attached to the adhesive part 23 and the like so as to overlap the one side adhesive piece 22a (or 22b).

<Crotch Section>

A shown in FIGS. 3 and 4, the crotch section 4 has, as an overall configuration, an almost strip shape extending in the front-to-rear direction when developed, and includes the front crotch part 4a, rear crotch part 4b and central crotch part 4c positioned midway between them, and is applied to the crotch of a wearer mainly setting the central crotch part 4c at the center. As shown in FIG. 5, the front crotch part 4a is bonded to the central front abdominal part 2c by the bonding part 18 while overlapping the interior side of the central front abdominal part 2c. As shown in FIG. 3, the rear crotch part 4b is bonded and fixed to the rear section 3 while overlapping the interior side of the rear section 3. Leg elastic members 40a and 40b are attached to the left edge 16a and right edge 16b of such crotch section 4 in a stretched state in the direction that the edges 16a and 16b extend.

Figure 6:
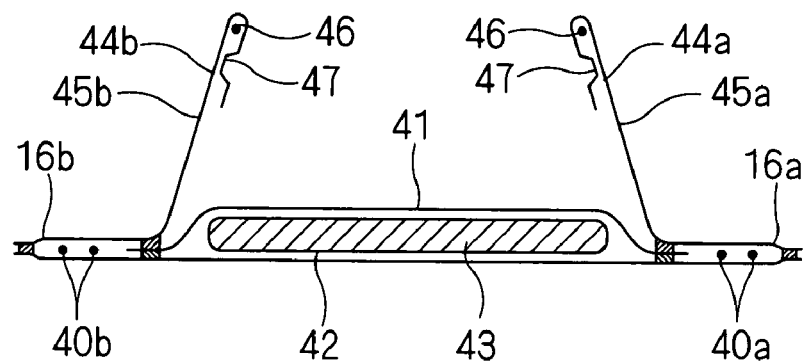
FIG. 6 is a sectional view taken along a line C2-C2 of the disposable pants shown in FIG. 3.

As shown in FIGS. 3 and 6, the crotch section 4 is formed by sandwiching the absorber 43 between a liquid-permeable top sheet 41 and a liquid-impermeable backsheet 42. The absorber 43 has a predetermined width and extends in the front-to-rear direction in the form of strip with the central crotch part 4c set at the center. The both left and right sides of the absorber 43 on the interior side of the crotch section 4 are provided with standing parts 44a and 44b extending in the direction that the crotch section 4 extends.

For instance, the top sheet 41 is made of a liquid-permeable nonwoven fabric or the like, and the backsheet 42 is made of a water-repellant nonwoven fabric or the like. The absorber 43 is formed, for example, by covering a mass of a hydrophilic fiber assembly layer such as crushed pulp fibers or cellulose fibers mixed with a particulate gelling agent, with a covering sheet such as a sheet of paper like tissue paper, a liquid-permeable nonwoven sheet or the like, and is formed in a predetermined shape.

As to areas of the top sheet 41 and backsheet 42 that do not overlap the absorber 43, surfaces facing each other are bonded to each other with an adhesive such as a hot melt adhesive. More preferably, as shown in FIG. 6, the width of the top sheet 41 is determined to cover the skin-facing side of the absorber 43 and to be slightly narrower than the width of the backsheet 42, and portions of the top sheet 41 extending off the absorber 43 in the front-to-rear and lateral directions are bonded to the backsheet 42 with an adhesive such as a hot melt adhesive. Left and right side sheets 45a and 45b constituting the standing parts 44a and 44b are bonded to the skin-facing side of portions of the backsheet 42 extending off the top sheet 41 in the both lateral directions with an adhesive such as a hot melt adhesive.

Further, as shown in FIG. 5, the both edges of the side sheets 45a and 45b in the front-to-rear direction are bonded to the both edges of the crotch section 4 in the front-to-rear direction with an adhesive 60 such as a hot melt adhesive. The laterally inside edges of the side sheets 45a and 45b are fixed by heating welding (or ultrasonic welding) or the like with sealing parts 47 so as to enclose elastic members 46 extending in the front-to-rear direction. The standing parts 44a and 44b have their laterally inside edges contracted by the contractive force of the elastic members 46, and are thereby raised in a direction to be pressed against the wearer's skin, as shown in FIG. 6.

Furthermore, in the present embodiment, as shown in FIG. 3, left and right edges of an area of the crotch section 4 that overlaps the front abdominal section 2 and a waist zone 3a of the rear section 3 are sloped edges 48a, 48b, 49a and 49b, and the area has a gradually tapered width toward its edge in the front-to-rear direction.

These sloped edges 48a and 48b prevent the front crotch part 4a from being hitched to curl up, become bent or affect the wearer's skin when raising/lowering the disposable pants 1, which allows smooth raising/lowering.

Further, the contractive force of the rear section 3 generally tends to decrease in an area where the rear section 3 and crotch section 4 overlap, however, forming a trim area by the aforementioned sloped edges 49a and 49b gradually increases the area of the elastic part of the rear section 3 toward the top side of the rear section 3, which allows the rear section 3 to easily fit the wearer's back.

Further, the adhesive members (or adhesive elements) 50 are provided on both sides of one edge of the crotch section 4 on the side of the front abdominal section 2 (cf. FIGS. 2 and 3). The adhesive members 50 are formed in the position facing the adhesive part 29 on the interior side of the adhesive pieces 22a and 22b. The adhesive members 50 are configured to be detachably attached to the adhesive part 29 on the interior side of the adhesive pieces 22a and 22b with the adhesive members 27 and 28 of the adhesive pieces 22a and 22b being attached to the aforementioned adhesive part 23 (cf. FIG. 8).

As a variation of the structure of the crotch section 4, the absorber 43 may be adhered to the skin-facing side of the sheet 42, rather than sandwiching the absorber 43 between the sheets 41 and 42, and the sheet 41 may be omitted. Alternatively, the absorber 43 with sheets bonded to its front and rear edges may be used as the crotch section 4, or a large absorber 43 may be used as the crotch section 4 and the sheets 41 and 42 may be omitted. Further, the absorber 43 may be formed as a separate member from the crotch section 4 to be attachable/detachable thereto/therefrom.

<Rear Section>

As shown in FIGS. 3 and 4, the rear section 3 has such a form that, when developed, left and right lower side corners of almost rectangle are cut almost diagonally, and is applied to an area from the waist to hips on the wearer's back. For this purpose, this rear section 3 includes the waist zone 3a in the form of almost laterally long strip in front view mainly positioned on the waist on the wearer's back and a hip zone 3b of almost trapezoidal form in front view joined downwardly to the waist zone 3a and mainly positioned on the wearer's hips.

A waist elastic member 51 is attached in a laterally stretched state to the upper edge 13 of the waist zone 3a. A body elastic member 52 is attached in a laterally stretched state to the other area of the waist zone 3a. A leg elastic member 53a is attached to the sloped edge 15a on the left lower side of the rear section 3 in a stretched state along the edge 15a. A leg elastic member 53b is attached to the sloped edge 15b on the right lower side of the rear section 3 in a stretched state along the edge 15b. Contraction and stretch of these elastic members 51, 52, 53a and 53b allows the rear section 3 to easily fit the wearer's back and hips.

Particularly, the hip zone 3b of the rear section 3 is formed to have a gradually tapered width downwardly and have their left and right sloped edges 15a and 15b provided with the leg elastic members 53a and 53b. Therefore, the hip zone 3b easily fits the wearer's hips when the edges 15a and 15b are contracted by the contractive forces of the leg elastic members 53a and 53b.

The leg elastic members 53a and 53b are continuously attached to the hip zone 3b along the left and right sloped edges 15a and 15b and lower edge 15c of the hip zone 3b, and then, at least an area 54 (cf. FIG. 4) overlapping the absorber 43 of the crotch section 4 is subjected to a weakening process. The weakening process is a process of cutting the elastic member in that area 54 or weakening its contractive force, or the like, to thereby bring about a no-tension state. This prevents the absorber 43 from causing an undesired contortion due to the contractive forces of the leg elastic members 53a and 53b and from degrading in its absorptive function.

<Other Structure and Material for Respective Parts, etc.>

As to the left and right elastic members 19a, 19b, elastic members 20a, 20b, and elastic members 21a, 21b provided in the front abdominal section 2, similarly to the case of the aforementioned leg elastic members 53a and 53b, it is preferable that the elastic members 20a, 20b, 21a and 21b be provided laterally continuously in the front abdominal section 2 through the central front abdominal part 2c, and then portions of the elastic members 20a, 20b, 21a and 21b positioned in the central front abdominal part 2c be subjected to the weakening process.

Further, the material for the adhesive pieces 22a and 22b may be selected appropriately from nonwoven fabrics, woven fabrics, knitted fabrics and plastic materials. Among them, a nonwoven fabric manufactured by one or a combination of a plurality of processes among spun-bond process, air-through process, point-bond process, melt-blow process and air-laid process is preferable. Further, a nonwoven fabric manufactured by a spun-bond process or SMS process combining the spun-bond process and melt-blow process with a weight of 30 to 100 g/m² is preferable in terms of strength. Most preferable is a nonwoven fabric manufactured by the spun-bond process with a weight of 50 to 85 g/m². The material can be selected appropriately from among synthetic fibers such as polypropylene, polyethylene, polyester, polyamide and the like and natural fibers such as pulp, silk and the like, but preferably, a synthetic fiber such as polypropylene, polyethylene or polyester can be used, and among them, one having a polypropylene or polyester fiber as its main component is strong and suitable. Most preferable one is a polyester fiber.

Further, for the elastic members 19a, 19b, 20a, 20b, 21a, 21b, 40a, 40b, 46, 53a and 53b, an elastic stretchable material (polyurethane thread, polyurethane film, natural rubber, etc.) typically used for disposable pants is employed, and is attached to a specified position of the pants 1 in a stretched state by adhering means such as a hot melt adhesive, heating welding, ultrasonic welding or the like.

The disposable pants 1 according to the present embodiment is structured as described above, and function as both pants and a diaper, which achieves easy raising/lowering when putting them on, and the like.

Since the adhesive pieces 22a and 22b are provided on the interior side of the front abdominal section 2, the breaking parts 17a and 17b can easily be recognized from outside without being obstructed by the adhesive pieces 22a and 22b. Further, when breaking at the breaking parts 17a and 17b, the adhesive pieces 22a and 22b are less likely to interfere with the breaking operation. This allows the breaking operation to be performed easily.

Further, the tabs 25 and 26 of the adhesive pieces 22a and 22b extending beyond the breaking parts 17a and 17b are folded to be folded back toward their body 24 sides. Accordingly, the breaking parts 17a and 17b extend without crossing over the adhesive pieces 22a and 22b. Hence, when breaking at the breaking parts 17a and 17b, the adhesive pieces 22a and 22b are less likely to obstruct the breaking operation with more efficacy. The breaking operation can be performed easily also in this respect.

Besides, for returning to the original state as pants after breaking the breaking parts 17a and 17b or when using as a disposable diaper, the adhesive members 27 and 28 provided on the tabs 25 and 26 may be detachably attached to the adhesive part 23, as shown in FIGS. 7 and 8. When attaching/detaching the tabs 25 and 26, the position of the tabs 25 and 26 is easily identified by the difference in colors because the tabs 25 and 26 are provided with the tab identification marks 32 colored differently from their neighboring members, that is, colored prominently. Herein, there are advantages of improved visibility of the tabs 25 and 26, easy and quick attachment/detachment of the tabs 25 and 26, namely, adhesive members 27 and 28 to/from the adhesive part 23, and improved workability in attaching/detaching.

Further, the tab identification marks 32 on the tabs 25 and 26 are easily provided by coloring them differently from their neighboring members or adhering a colored tape, which can advantageously be provided at low costs.

Second Embodiment

Figure 9:
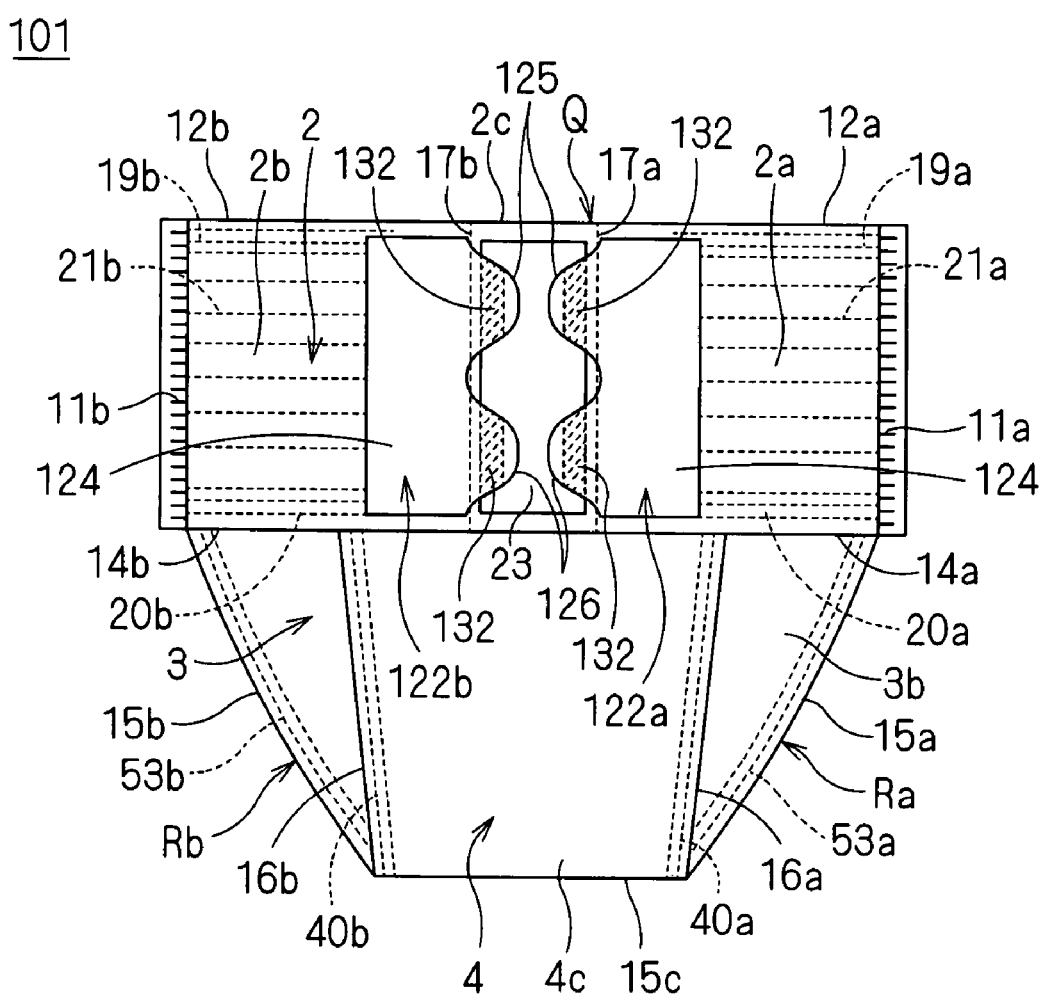
FIG. 9 is a front view of disposable pants according to a second embodiment of the present invention.
Figure 10:
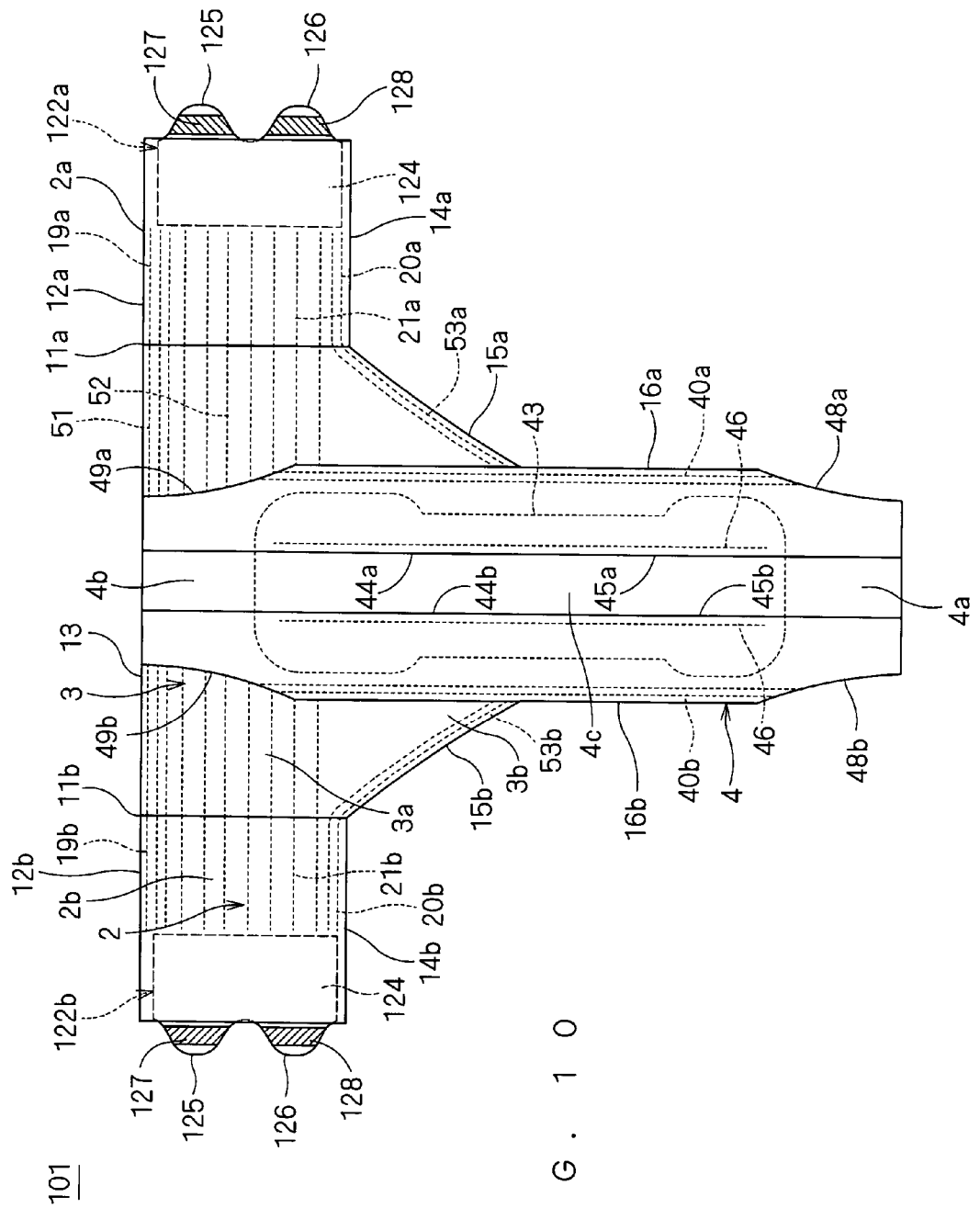
FIG. 10 is a diagram showing a developed state.
Figure 11:
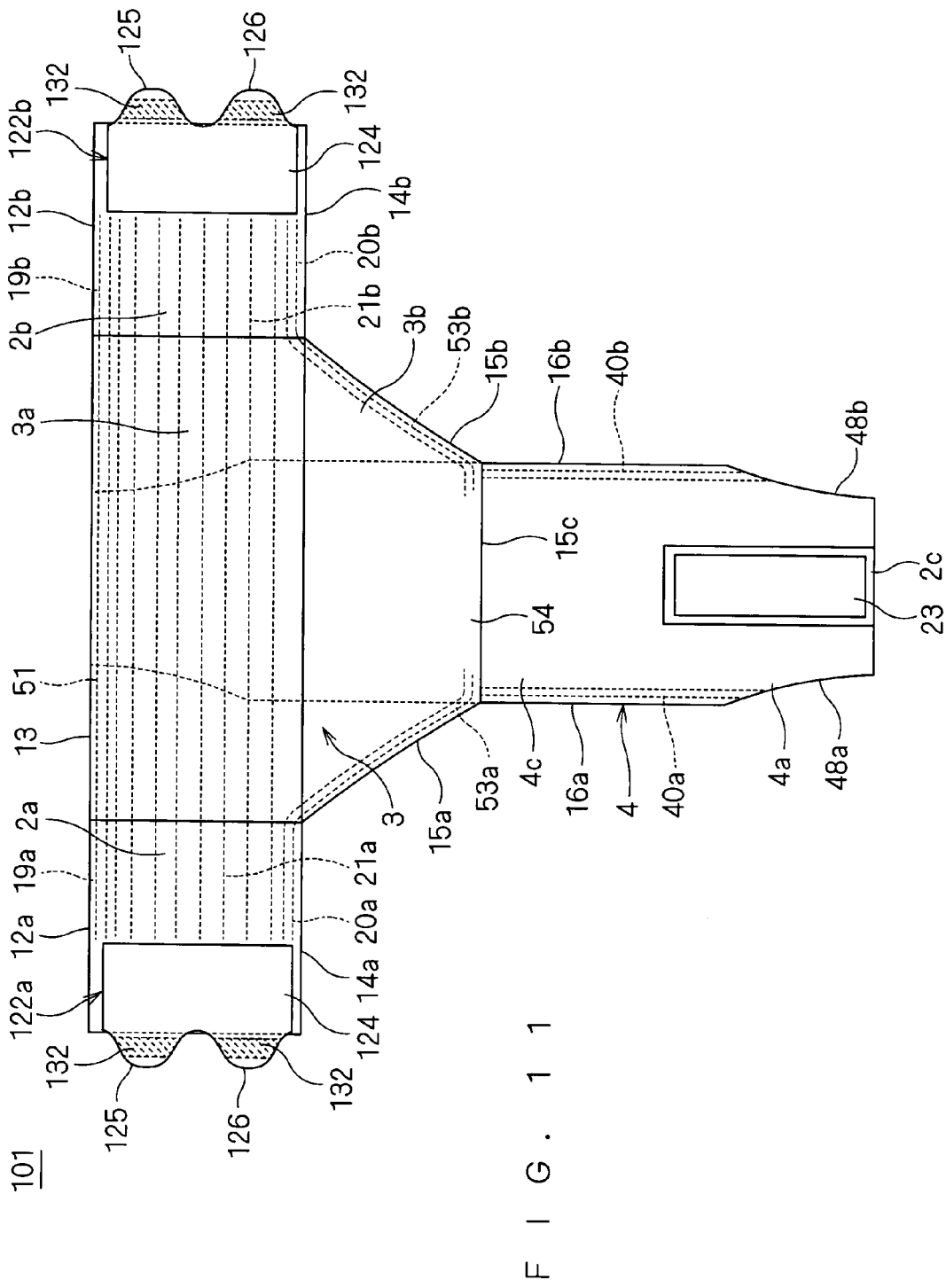
FIG. 11 is a diagram of the disposable pants shown in FIG. 10 as viewed from the opposite side to FIG. 10.

With reference to FIGS. 9 to 11, disposable pants 101 according to a second embodiment of the present invention will be described. This second embodiment will be addressed to a form in which adhesive pieces 122a and 122b are provided on the exterior side of the front abdominal section 2. In the description of the second embodiment, similar components as those described in the first embodiment are indicated by the same reference numerals, and their explanations are omitted.

In the disposable pants 101 according to this second embodiment, instead of providing the adhesive pieces 22a and 22b on the interior side of the left front abdominal part 2a and right front abdominal part 2b as in the first embodiment, the adhesive pieces 122a and 122b are provided on the exterior side of the left front abdominal part 2a and right front abdominal part 2b.

More specifically, the adhesive pieces 122a and 122b have a similar structure as the aforementioned adhesive pieces 22a and 22b, and each include an almost vertically long strip body 124 and two tabs 125 and 126 bifurcated one on top of the other extending from the body 124 toward its free edge side.

The laterally outside edges of the body 124 are bonded to areas short of the edges of the left front abdominal part 2a and right front abdominal part 2b on their exterior side and on the side of the breaking parts 17a and 17b by the adhesive 66, e.g., hot melt adhesive.

Besides, the tabs 125 and 126 of the adhesive pieces 122a and 122b that extend beyond the breaking parts 17a and 17b are detachably attached to the adhesive part 23 on the central front abdominal part 2c with the adhesive members 127 and 128 provided on their interior side interposed therebetween.

In the present embodiment, the adhesive members 127 and 128 are adhered with a colored adhesive such as a hot melt adhesive previously colored in green or the like when attaching and fixing them to the tabs 125 and 126, and the color of the hot melt adhesive is seen from the exterior side of the tabs 125 and 126 to serve as tab identification marks 132 that can be identified from their neighboring members of similar colors such as white, for example.

In the disposable pants 101, the aforementioned adhesive parts 29 and 50 are omitted.

When the disposable pants 101 are used as pants, the breaking parts 17a and 17b are not broken, and are kept in the form at the shipping stage.

On the other hand, when the disposable pants 101 are used as a diaper, they are developed by breaking the breaking parts 17a and 17b, and when worn again, the adhesive members 127 and 128 on the tabs 125 and 126 are detachably attached to the adhesive part 23.

In the present embodiment, similarly to the first embodiment, the tabs 125 and 126 are also provided with the tab identification marks 132 colored differently from their neighboring members, that is, colored prominently. When attaching/detaching the tabs 125 and 126, the position of the tabs 125 and 126 is easily identified by the difference in colors, which produces advantages of easy and quick attachment/detachment of the tabs 125 and 126, namely, adhesive members 127 and 128 to/from the adhesive part 23 and improved workability in attaching/detaching.

Further, the tab identification marks 132 are provided by using a colored adhesive colored differently from their neighboring members as an adhesive for adhering and fixing the adhesive members 127 and 128 to the tabs 125 and 126. This allows the tab identification marks 132 to be obtained concurrently with the step of adhering the adhesive pieces 127 and 128 to the tabs 125 and 126, eliminating an additional step of providing the tab identification marks 132, which results in excellent production efficiency.

The above-described embodiments describe the structure provided with the tab identification marks 32, 132 by providing partially-colored portions on the tabs 25, 26, 125, 126, however, the tab identification marks 32 and 132 may be provided by coloring the tabs 25, 26, 125, 126 as a whole, or alternatively, may be provided by edging or drawing a pattern thereon to allow identification from their neighboring members.

The tab identification marks 32 and 132 may be edged by frill, for example, or may have a pattern drawn thereon, rather than being colored, to achieve identification from their neighboring members. Further, the tabs 25, 26, 125, 126 themselves may be made of material of different color to serve as the tab identification marks 32 and 132.

Further, when the front abdominal section 2, rear section 3, crotch section 4, and adhesive part 23 are made of colored material such as brown, the adhesive pieces 22a and 22b may be made of a material of color such as white different from their neighboring members to allow the tabs 25, 26, 125, 126 themselves to serve as the tab identification marks 32 and 132.

Further, in the second embodiment, a colored adhesive colored differently from other members is used as an adhesive for adhering and fixing the adhesive members 127 and 128 to provide the tabs 125 and 126 with the tab identification marks 132, however, the adhesive members 127 and 128 themselves attached and fixed to the tabs 125 and 126 by adhesion or the like may be made of material of different color from other members, so that the adhesive members 127 and 128 whose color is seen through the tabs 125 and 126 serve as the tab identification marks 132. In this case, effects similar to the second embodiment can be obtained.

Further, it has been shown that the upper and lower tabs 25, 26, 125, 126 are each provided with the tab identification marks 32 and 132, however, either upper or lower tabs 25, 26, 125, 126 may be provided with the tab identification marks 32 and 132.

Furthermore, it has been shown that the adhesive pieces 22a, 22b, 122a, 122b are each provided with a pair of upper and lower tabs 25, 26, 125, 126, but may each be provided with a single tab, or three or more tabs. The invention is not limited to the number and shape described in the above embodiments.

The invention claimed is:

1. Disposable pants comprising:
a front abdominal section;
a rear section joined to said front abdominal section to form a substantially annular structure;
a crotch section including an absorber, said crotch section joined between said front abdominal section and said rear section;
a left breaking part and a right breaking part provided, respectively, on a left side and a right side of an area of said front abdominal section to which said crotch section is joined;
a left adhesive piece and a right adhesive piece bonded on said front abdominal section to a left laterally outward side of said left breaking part and a right laterally outward side of said right breaking part, respectively;
an adhesive part provided between said left breaking part and said right breaking part on an exterior side of said front abdominal section, said left adhesive piece and said right adhesive piece being attachable to and/or detachable from said adhesive part;
a left tab and a right tab provided, respectively, on said left adhesive piece and said right adhesive piece for attachment to and/or detachment from said adhesive part;
a left tab identification mark and a right tab identification mark provided, respectively, on said left adhesive piece and said right adhesive piece; and
a left adhesive member and a right adhesive member being attachable to and/or detachable from said adhesive part,
wherein each of said left breaking part and said right breaking part has an attached state and a broken state, and each of said left adhesive piece and said right adhesive piece is disposed between an exterior surface of said disposable pants and a skin-facing surface of said disposable pants when said left breaking part and said right breaking part are in said attached state, and
wherein said left tab identification mark and said right tab identification mark are each made of a colored adhesive for adhering and fixing said left adhesive member and said right adhesive member to said left tab and said right tab, respectively.

2. The disposable pants of claim 1, wherein the left tab and the right tab include the left adhesive member and the right adhesive member, respectively; and
said left adhesive member and said right adhesive member are attachable to and detachable from said adhesive part.

3. The disposable pants of claim 1, further comprising:
a left adhesive element and a right adhesive element disposed on said front abdominal section on a left side and a right side of said adhesive part, respectively;
wherein said left adhesive piece contacts said left adhesive element when said left adhesive member is attached to said adhesive part and said right adhesive piece contacts said right adhesive element when said right adhesive member is attached to said adhesive part.

4. Disposable pants comprising:
a front abdominal section;
a rear section joined to said front abdominal section to form a substantially annular structure;
a crotch section including an absorber, said crotch section joined between said front abdominal section and said rear section;
a left breaking part and a right breaking part provided, respectively, on a left side and a right side of an area of said front abdominal section to which said crotch section is joined;

a left adhesive piece and a right adhesive piece bonded on said front abdominal section to a left laterally outward side of said left breaking part and a right laterally outward side of said right breaking part, respectively;
an adhesive part provided between said left breaking part and said right breaking part on an exterior side of said front abdominal section, said left adhesive piece and said right adhesive piece being attachable to and/or detachable from said adhesive part;
a left tab and a right tab provided, respectively, on said left adhesive piece and said right adhesive piece for attachment to and/or detachment from said adhesive part;
a left tab identification mark and a right tab identification mark provided, respectively, on said left adhesive piece and said right adhesive piece; and
a left adhesive member and a right adhesive member being attachable to and/or detachable from said adhesive part,
wherein each of said left breaking part and said right breaking part has an attached state and a broken state, and each of said left adhesive piece and said right adhesive piece is sandwiched between said front abdominal section and said crotch section when said left breaking part and said right breaking part are in said attached state, and
wherein said left tab identification mark and said right tab identification mark are each made of a colored adhesive for adhering and fixing said left adhesive member and said right adhesive member to said left tab and said right tab, respectively.

5. Disposable pants comprising:
a front abdominal section;
a rear section joined to said front abdominal section to form a substantially annular structure;
a crotch section including an absorber, said crotch section joined between said front abdominal section and said rear section;
a left breaking part and a right breaking part provided, respectively, on a left side and a right side of an area of said front abdominal section to which said crotch section is joined;
a left adhesive piece and a right adhesive piece bonded on said front abdominal section to a left laterally outward side of said left breaking part and a right laterally outward side of said right breaking part, respectively;
an adhesive part provided between said left breaking part and said right breaking part on an exterior side of said front abdominal section, said left adhesive piece and said right adhesive piece being attachable to and/or detachable from said adhesive part;
a left tab and a right tab provided, respectively, on said left adhesive piece and said right adhesive piece for attachment to and/or detachment from said adhesive part;
a left tab identification mark and a right tab identification mark provided, respectively, on said left adhesive piece and said right adhesive piece; and
a left adhesive member and a right adhesive member being attachable to and/or detachable from said adhesive part,
wherein each of said left breaking part and said right breaking part has an attached state and a broken state, and each of said left tab and said right tab is sandwiched between said front abdominal section and said crotch section when said left breaking part and said right breaking part are in said attached state, and
wherein said left tab identification mark and said right tab identification mark are each made of a colored adhesive for adhering and fixing said left adhesive member and said right adhesive member to said left tab and said right tab, respectively.

6. The disposable pants of claim 1, wherein each of said left tab and said right tab is disposed between an exterior surface of said disposable pants and a skin-facing surface of said disposable pants when said left breaking part and said right breaking part are in said attached state.

7. Disposable pants comprising:
a front abdominal section;
a rear section joined to said front abdominal section to form a substantially annular structure;
a crotch section including an absorber, said crotch section joined between said front abdominal section and said rear section;
a left breaking part and a right breaking part provided on a left side and a right side, respectively, of an area of said front abdominal section to which said crotch section is joined;
a left adhesive piece and a right adhesive piece bonded on said front abdominal section to a left laterally outward side of said left breaking part and a right laterally outward side of said right breaking part, respectively;
an adhesive part provided between said left breaking part and said right breaking part on an exterior side of said front abdominal section, said left adhesive piece and said right adhesive piece being attachable to and/or detachable from said adhesive part;
a left tab and a right tab provided, respectively, on said left adhesive piece and said right adhesive piece for attachment to and/or detachment from said adhesive part; and
a left tab identification mark and a right tab identification mark provided, respectively, on said left adhesive piece and said right adhesive piece,
wherein each of said left breaking part and said right breaking part has an attached state and a broken state, and each of said left adhesive piece and said right adhesive piece is disposed between an exterior surface of said disposable pants and a skin-facing surface of said disposable pants when said left breaking part and said right breaking part are in said attached state, and
wherein said left tab identification mark and said right tab identification mark are each a linearly colored part.

8. The disposable pants of claim 7, wherein each of said left tab identification mark and said right tab identification mark comprise at least one linear elongated piece extending lengthwise from a bottom edge of said left tab and said right tab toward a top edge of said left tab and said right tab.

9. The disposable pants of claim 7, further comprising:
a left adhesive member and a right adhesive member provided on said left tab and said right tab, respectively, said left adhesive member and said right adhesive member each being attachable to and detachable from said adhesive part; and
a left adhesive element and a right adhesive element disposed on said front abdominal section on a left side and a right side of said adhesive part, respectively;
wherein said left adhesive piece contacts said left adhesive element when said left adhesive member is attached to said adhesive part and said right adhesive piece contacts said right adhesive element when said right adhesive member is attached to said adhesive part.

10. Disposable pants comprising:
a front abdominal section;
a rear section joined to said front abdominal section to form a substantially annular structure;
a crotch section including an absorber, said crotch section joined between said front abdominal section and said rear section;

a left breaking part and a right breaking part provided on a left side and a right side, respectively, of an area of said front abdominal section to which said crotch section is joined;

a left adhesive piece and a right adhesive piece bonded on said front abdominal section to a left laterally outward side of said left breaking part and a right laterally outward side of said right breaking part, respectively;

an adhesive part provided between said left breaking part and said right breaking part on an exterior side of said front abdominal section, said left adhesive piece and said right adhesive piece being attachable to and/or detachable from said adhesive part;

a left tab and a right tab provided, respectively, on said left adhesive piece and said right adhesive piece for attachment to and/or detachment from said adhesive part; and a left tab identification mark and a right tab identification mark provided, respectively, on said left adhesive piece and said right adhesive piece, wherein each of said left breaking part and said right breaking part has an attached state and a broken state, and each of said left adhesive piece and said right adhesive piece is sandwiched between said front abdominal section and said crotch section when said left breaking part and said right breaking part are in said state, and wherein said left tab identification mark and said right tab identification mark are each a linearly colored part.

11. Disposable pants comprising:

a front abdominal section;

a rear section joined to said front abdominal section to form a substantially annular structure;

a crotch section including an absorber, said crotch section joined between said front abdominal section and said rear section;

a left breaking part and a right breaking part provided on a left side and a right side, respectively, of an area of said front abdominal section to which said crotch section is joined;

a left adhesive piece and a right adhesive piece bonded on said front abdominal section to a left laterally outward side of said left breaking part and a right laterally outward side of said right breaking part, respectively;

an adhesive part provided between said left breaking part and said right breaking part on an exterior side of said front abdominal section, said left adhesive piece and said right adhesive piece being attachable to and/or detachable from said adhesive part;

a left tab and a right tab provided, respectively, on said left adhesive piece and said right adhesive piece for attachment to and/or detachment from said adhesive part; and a left tab identification mark and a right tab identification mark provided, respectively, on said left adhesive piece and said right adhesive piece, wherein each of said left breaking part and said right breaking part has an attached state and a broken state, and each of said left tab and said right tab is sandwiched between said front abdominal section and said crotch section when said left breaking part and said right breaking part are in said attached state, and wherein said left tab identification mark and said right tab identification mark are each a linearly colored part.

12. The disposable pants of claim 7, wherein each of said left tab and said right tab is disposed between an exterior surface of said disposable pants and a skin-facing surface of said disposable pants when said left breaking part and said right breaking part are in said attached state.

13. Disposable pants comprising:

a front abdominal section;

a rear section joined to said front abdominal section to form a substantially annular structure;

a crotch section including an absorber, said crotch section joined between said front abdominal section and said rear section;

a left breaking part and a right breaking part provided on a left side and a right side, respectively, of an area of said front abdominal section to which said crotch section is joined;

a left adhesive piece and a right adhesive piece bonded on said front abdominal section to a left laterally outward side of said left breaking part and a right laterally outward side of said right breaking part, respectively;

an adhesive part provided between said left breaking part and said right breaking part on an exterior side of said front abdominal section, said left adhesive piece and said right adhesive piece being attachable to and/or detachable from said adhesive part;

a left tab and a right tab provided, respectively, on said left adhesive piece and said right adhesive piece for attachment to and/or detachment from said adhesive part; and a left tab identification mark and a right tab identification mark provided, respectively, on said left adhesive piece and said right adhesive piece; and a left adhesive member and a right adhesive member each being attachable to and/or detachable from said adhesive part, wherein each of said left breaking part and said right breaking part has an attached state and a broken state, and each of said left adhesive piece and said right adhesive piece is disposed between an exterior surface of said disposable pants and a skin-facing surface of said disposable pants when said left breaking part and said right breaking part are in said attached state, and wherein said left adhesive member and said right adhesive member are disposed, respectively, on said left tab and said right tab, distal from a tip portion of each of said left tab and said right tab such that said tip portions of said left tab and said right tab are exposed.

14. The disposable pants of claim 13, wherein said tip portion of each of said left tab and said right tab is not covered by said left adhesive member or said right adhesive member.

15. The disposable pants of claim 13, further comprising:

a left adhesive element and a right adhesive element disposed on said front abdominal section on a left side and a right side of said adhesive part, respectively;

wherein said left adhesive piece contacts said left adhesive element when said left adhesive member is attached to said adhesive part and said right adhesive piece contacts said right adhesive element when said right adhesive member is attached to said adhesive part.

16. Disposable pants comprising:

a front abdominal section;

a rear section joined to said front abdominal section to form a substantially annular structure;

a crotch section including an absorber, said crotch section joined between said front abdominal section and said rear section;

a left breaking part and a right breaking part provided on a left side and a right side, respectively, of an area of said front abdominal section to which said crotch section is joined;

a left adhesive piece and a right adhesive piece bonded on said front abdominal section to a left laterally outward side of said left breaking part and a right laterally outward side of said right breaking part, respectively;

an adhesive part provided between said left breaking part and said right breaking part on an exterior side of said front abdominal section, said left adhesive piece and said right adhesive piece being attachable to and/or detachable from said adhesive part;

a left tab and a right tab provided, respectively, on said left adhesive piece and said right adhesive piece for attachment to and/or detachment from said adhesive part; and a left tab identification mark and a right tab identification mark provided, respectively, on said left adhesive piece and said right adhesive piece; and a left adhesive member and a right adhesive member each being attachable to and/or detachable from said adhesive part, wherein each of said left breaking part and said right breaking part has an attached state and a broken state, and each of said left adhesive piece and said right adhesive piece is sandwiched between said front abdominal section and said crotch section when said left breaking part and said right breaking part are in said attached state, and wherein said left adhesive member and said right adhesive member are disposed, respectively, on said left tab and said right tab, distal from a tip portion of each of said left tab and said right tab such that said tip portions of said left tab and said right tab are exposed.

17. Disposable pants comprising:

a front abdominal section;

a rear section joined to said front abdominal section to form a substantially annular structure;

a crotch section including an absorber, said crotch section joined between said front abdominal section and said rear section;

a left breaking part and a right breaking part provided on a left side and a right side, respectively, of an area of said front abdominal section to which said crotch section is joined;

a left adhesive piece and a right adhesive piece bonded on said front abdominal section to a left laterally outward side of said left breaking part and a right laterally outward side of said right breaking part, respectively;

an adhesive part provided between said left breaking part and said right breaking part on an exterior side of said front abdominal section, said left adhesive piece and said right adhesive piece being attachable to and/or detachable from said adhesive part;

a left tab and a right tab provided, respectively, on said left adhesive piece and said right adhesive piece for attachment to and/or detachment from said adhesive part; and a left tab identification mark and a right tab identification mark provided, respectively, on said left adhesive piece and said right adhesive piece; and a left adhesive member and a right adhesive member each being attachable to and/or detachable from said adhesive part, wherein each of said left breaking part and said right breaking part has an attached state and a broken state, and each of said left tab and said right tab is sandwiched between said front abdominal section and said crotch section when said left breaking part and said right breaking part are in said state, and wherein said left attached adhesive member and said right adhesive member are disposed, respectively, on said left tab and said right tab, distal from a tip portion of each of said left tab and said right tab such that said tip portions of said left tab and said right tab are exposed.

* * * * *